(12) United States Patent
Maeda et al.

(10) Patent No.: US 9,353,392 B2
(45) Date of Patent: May 31, 2016

(54) METHOD FOR PRODUCING INDIGESTIBLE DEXTRIN

(71) Applicant: Matsutani Chemical Industry Co., Ltd., Itami-shi, Hyogo (JP)

(72) Inventors: Yoshiaki Maeda, Itami (JP); Kensaku Shimada, Minoh (JP); Yasuo Katta, Akashi (JP)

(73) Assignee: MATSUTANI CHEMICAL INDUSTRY CO., LTD., Itami-Shi, Hyogo (JP)

(*) Notice: Subject to any disclaimer, the term of this patent is extended or adjusted under 35 U.S.C. 154(b) by 0 days.

(21) Appl. No.: 14/667,720

(22) Filed: Mar. 25, 2015

(65) Prior Publication Data
US 2015/0275253 A1    Oct. 1, 2015

(30) Foreign Application Priority Data

Mar. 26, 2014  (JP) ................... 2014-063795

(51) Int. Cl.
| | | |
|---|---|---|
| *C12P 19/14* | (2006.01) | |
| *A23L 1/308* | (2006.01) | |
| *C12P 19/02* | (2006.01) | |
| *C08B 30/18* | (2006.01) | |
| *C12P 19/04* | (2006.01) | |
| *C13K 1/06* | (2006.01) | |

(52) U.S. Cl.
CPC .............. *C12P 19/14* (2013.01); *A23L 1/3088* (2013.01); *C08B 30/18* (2013.01); *C12P 19/02* (2013.01); *C12P 19/04* (2013.01); *C13K 1/06* (2013.01); *A23V 2002/00* (2013.01)

(58) Field of Classification Search
CPC ... A23L 1/3088; A23V 2002/00; C12P 19/02; C12P 19/14; C12P 19/04; C13K 1/06; C08B 30/18
See application file for complete search history.

(56) References Cited

U.S. PATENT DOCUMENTS

| | | | |
|---|---|---|---|
| 4,622,233 A | 11/1986 | Torres | |
| 5,364,652 A * | 11/1994 | Ohkuma | A23C 9/13 426/549 |
| 5,573,794 A | 11/1996 | Duflot | |
| 5,601,863 A | 2/1997 | Borden et al. | |
| 2003/0096055 A1 | 5/2003 | Fuertes | |
| 2011/0171709 A1* | 7/2011 | Bardsley | C12P 7/10 435/165 |

FOREIGN PATENT DOCUMENTS

| | | |
|---|---|---|
| JP | 7-196703 A | 8/1995 |
| JP | 2003-183304 A | 7/2003 |
| WO | 92/14761 A1 | 9/1992 |

OTHER PUBLICATIONS

Dey T.B. et al., "Application of decolourized and partially purified polygalacturonase and alpha-amylase in apple juice clarification", Brazilian Journal of Microbiology, Published online on May 19, 2014, vol. 45, No. 1, pp. 97-104.*
Rani A.S. et al., Preparation and characterization of amyloglucosidase adsorbed on activated charcoal, Journal of Molecular Catalysis B: Enzymatic, 2000, vol. 10, pp. 471-476.*
Kuba Y. et al., Production of cello-oligosaccharides by enzymatic hydrolysis in the presence of activated carbon, Enzyme Microb. Technol., 1990, vol. 12, pp. 72-75.*
Kazuhiro Okuma, et al, "Production of Indigestible Dextrin from Pyrodextrin", J. Appl. Glycosci, 2003, pp. 389-394, vol. 50, The Japanese Society of Applied Glycoscience, English abstract only.

* cited by examiner

*Primary Examiner* — Satyendra K Singh
(74) *Attorney, Agent, or Firm* — Nath, Goldberg & Meyer; Joshua B. Goldberg; Tanya E. Harkins

(57) ABSTRACT

The present invention provides a method for producing indigestible dextrin which is inexpensive and can simply and efficiently suppress coloring. The method for producing indigestible dextrin includes the steps of liquefying pyrodextrin and saccharifying pyrodextrin, wherein at least one of the liquefying step and the saccharifying step is performed in the presence of activated carbon.

4 Claims, No Drawings

METHOD FOR PRODUCING INDIGESTIBLE DEXTRIN

FIELD OF THE INVENTION

The present invention relates to a method for producing indigestible dextrin, particularly to a method for producing indigestible dextrin which is inexpensive and can simply and efficiently suppress coloring.

DESCRIPTION OF THE RELATED ART

Indigestible dextrin has various physiological functions such as an action for moderating absorption of neutral fat and sugar after a meal and an action for controlling intestinal function and is widely utilized for health food such as a food for specified health use. In particular, the indigestible dextrin is used in about ⅓ of the whole food for specified health use. Further, the indigestible dextrin is a material widely utilized for general food for the purpose of mouthfeel improvement and reform of food, such as imparting thick feeling, masking, improving quality of taste, and holding flavor.

Indigestible dextrin is produced by allowing α-amylase and glucoamylase which are hydrolytic enzymes to act on pyrodextrin prepared by adding a very small amount of hydrochloric acid to starch followed by heating, which is followed by a purification step such as decoloring and desalting. In the step of heating starch (roasting step) and the hydrolysis step of liquefying and saccharifying pyrodextrin in the production process, many colored substances are produced by heating and caramelization and the Maillard reaction accompanying the heating. Although activated carbon and an ion-exchange resin are used for removing a colored substance after completion of the reaction (refer to J. Appl. Glycosci., 50, 389-394 (2003)), a large load will be applied to the purification step if the degree of coloring is high. Further, when purification is insufficient, the quality of indigestible dextrin which is a finished product will also be affected. This causes an increase in production cost and a reduction in the quality of indigestible dextrin, and an improvement thereof is desired.

U.S. Pat. No. 4,622,233 describes a decoloring method using a bleaching agent such as hydrogen peroxide, benzoyl peroxide, and sodium chlorite as a method for purifying polydextrose which is produced by heating and condensing glucose, sorbitol, and citric acid. Although a decoloring effect by a bleaching agent can be expected by this method, there is a danger that the structure itself will be changed because a carbonyl group is produced in the molecule by oxidation reaction at the same time.

Further, Japanese Patent Laid-Open No. 7-196703 describes a method for oxidizing polyglucose, polydextrose, and pyrodextrin by glucose oxidase followed by treatment with a hydroxyl-type anion exchanger as a method for purifying a low-calorie glucose polymer. However, the enzyme reaction by glucose oxidase is a method requiring much time and labor and cost in that air needs to be passed through a tank by aeration or the like, and in that a reduction in pH needs to be always controlled by sodium hydroxide or the like.

Further, International Publication No. WO 92/14761 and Japanese Patent Laid-Open No. 2003-183304 describe a method of hydrogenation in the presence of a catalyst such as Raney nickel as a method for decoloring polydextrose and a fiber-containing soluble starch derivative. Although hydrogenation itself is a technique used for many foods such as maltitol and reduced starch syrup, hydrogenation produces a different material because a reducing terminal is alcoholized by hydrogenation. Further, hydrogenation and subsequent purification requires additional cost.

An object of the present invention is to provide a method for producing indigestible dextrin which is inexpensive and can simply and efficiently suppress coloring.

SUMMARY OF THE INVENTION

As a result of extensive and intensive studies to achieve the above object, the present inventors have found that the coloring of a product is significantly suppressed by performing at least one of a liquefying step and a saccharifying step in the presence of activated carbon in the production process of indigestible dextrin and completed this invention.

That is, the present invention provides the following inventions.

(1) A method for producing indigestible dextrin comprising the steps of liquefying pyrodextrin and saccharifying pyrodextrin, wherein at least one of the liquefying step and the saccharifying step is performed in the presence of activated carbon.

(2) The method according to the above (1), wherein the step of liquefying pyrodextrin is performed in the presence of activated carbon.

(3) The method according to the above (2), wherein the step of liquefying pyrodextrin is a step of heating an aqueous solution of pyrodextrin.

(4) The method according to the above (2), wherein the step of liquefying pyrodextrin is a step of hydrolyzing an aqueous solution of pyrodextrin with α-amylase.

(5) The method according to the above (1), wherein the step of saccharifying pyrodextrin is performed in the presence of activated carbon.

(6) The method according to the above (5), wherein the step of saccharifying pyrodextrin is a step of hydrolyzing a liquefied solution of pyrodextrin using glucoamylase alone or glucoamylase in combination with α-amylase.

According to the present invention, at least one of a liquefying step and a saccharifying step in the production process of indigestible dextrin is performed in the presence of activated carbon, thereby capable of providing a production method which is inexpensive and can simply and efficiently suppress coloration of indigestible dextrin.

DETAILED DESCRIPTION OF THE PREFERRED EMBODIMENTS

The method for producing indigestible dextrin of the present invention is a method comprising the steps of liquefying pyrodextrin and saccharifying pyrodextrin, wherein at least one of the liquefying step and the saccharifying step is performed in the presence of activated carbon.

The indigestible dextrin in the present invention refers to dextrin containing an indigestible component measured by high performance liquid chromatography (an enzyme-HPLC method) which is the analytical method of dietary fiber described in EISHIN No. 13 (Analytical Methods for Nutrients on the Standards for Nutrition Labeling)The indigestible component is preferably contained in an amount of 85 to 95 mass %, more preferably 90 to 95 mass %.

The pyrodextrin in the present invention refers to a material having a whiteness of about 55 to 65 and an indigestible component content of about 50 to 65 mass % which is obtained by adding several mass % of mineral acid such as sulfuric acid, nitric acid, and hydrochloric acid to raw material starch such as corn, wheat, cassava, and potato (for example, 0.03 to 0.1 mass % of mineral acid relative to the mass of raw material starch), preliminary drying the mixture to a water content of about 3%, and then heating the dried mixture at about 130° C. to 180° C.

In the present invention, the "liquefying step" refers to a step of heating an aqueous solution of pyrodextrin at a high temperature of about 80 to 115° C. in the presence or absence of activated carbon, and the step can optionally include a step of hydrolyzing pyrodextrin with a liquefying enzyme such as α-amylase. Examples of a specific apparatus include a jet cooker and a batch-type pressurized steam-cooker.

In the present invention, the "saccharifying step" refers to a step of adding glucoamylase alone or glucoamylase in combination with α-amylase to a liquefied solution of pyrodextrin in the presence or absence of activated carbon to thereby hydrolyze digestible components in dextrin to glucose. Generally, the reaction is performed batchwise using a saccharification tank.

The "activated carbon" as used in the present invention is not particularly limited, but powdered activated carbon is preferred in terms of handleability. Examples of activated carbon that can be used include steam-activated carbon which is activated with a gas and zinc chloride-activated carbon which is activated with a chemical, and zinc chloride-activated carbon is preferred.

In the present invention, the "degree of coloring" refers to a value obtained by measuring the absorbances at 420 nm and at 720 nm of a 10 mass % sample solution with a spectrophotometer using a 1-cm cell, respectively, and multiplying the difference between the absorbances 10 times.

Hereinafter, the production method of the present invention will be described in detail.

In the present invention, the "liquefying step" further includes two types: a "liquefying step using enzyme" (that is, a liquefying step including a digesting step by enzyme) and a "liquefying step without using enzyme" (that is, a liquefying step which does not include a digesting step by enzyme).

In performing the liquefying step which does not include enzyme digestion, an aqueous solution of pyrodextrin, preferably 35 to 40 mass % aqueous solution, is first prepared, and the pH of the aqueous solution of pyrodextrin is preferably adjusted to 4.0 to 4.7, more preferably to 4.3 to 4.5, with a pH adjuster such as sodium hydroxide.

In performing the liquefying step including enzyme digestion, an aqueous solution of pyrodextrin, preferably 35 to 40 mass % aqueous solution, is first prepared, and the pH of the aqueous solution of pyrodextrin is preferably adjusted to 5.3 to 6.3, more preferably to 5.5 to 5.8, with a pH adjuster such as sodium hydroxide. Subsequently, α-amylase, for example, may be added in an amount of 0.05 to 0.2 mass % relative to the solid content of pyrodextrin.

Subsequently, both the aqueous solutions are heated in the presence or absence of activated carbon using a heating apparatus such as a jet cooker and a batch-type pressurized steam-cooker preferably at 80 to 115° C., more preferably at 90 to 110° C., further preferably at 95 to 105° C., preferably for about 15 to 60 minutes, more preferably for about 30 to 60 minutes to thereby liquefy pyrodextrin. When α-amylase is used, the temperature is then optionally increased to about 120 to 130° C. to deactivate α-amylase.

Before starting the "saccharifying step," a cooled liquefied solution of pyrodextrin is, for example, transferred to a saccharification tank to adjust the pH preferably to 4.3 to 4.7 with a pH adjuster such as sodium hydroxide and hydrochloric acid. When enzyme digestion has not been performed in the liquefying step, it is preferred to add α-amylase in an amount of 0.05 to 0.2 mass % relative to the solid content and glucoamylase in an amount of 0.1 to 1.0 mass % relative to the solid content.

When enzyme digestion has been performed in the "liquefying step," glucoamylase alone is preferably added in an amount of 0.1 to 1.0 mass % relative to the solid content.

Further, when the liquefying step has been performed in the absence of activated carbon, activated carbon is added to the liquefied solution of pyrodextrin (the solution subjected to the above liquefying step), and the mixture is digested preferably at 50 to 70° C., more preferably at 55 to 65° C. for 3 to 48 hours, further preferably at the same temperature for 6 to 24 hours, to thereby hydrolyze digestible carbohydrate to glucose.

The amount of activated carbon added is not particularly limited, but a too large amount leads to a load from a cost aspect or in a filtration step, and a too small amount results in little effect. Therefore, activated carbon is added in an amount of preferably 0.1 to 5.0 mass %, more preferably 0.5 to 4.0 mass %, further preferably 1.0 to 4.0 mass %, relative to the solid content.

Further, when activated carbon is added in an amount in the range of 1.0 to 2.5 mass %, the coloring suppression effect by the method of the present invention is remarkable as compared with the coloring suppression effect by a conventional method in which activated carbon is added after Saccharification. Therefore, the method of the present invention is particularly effective when the amount of activated carbon is desired to be limited to a low level.

Further, if activated carbon is present during an enzyme reaction, it is expected that the enzyme reaction is inhibited by adsorption. However, unexpectedly, no difference is observed between the amount of glucose finally produced in the presence of activated carbon and that in the absence of activated carbon. Note that when the liquefying step is performed in the presence of activated carbon, the addition of activated carbon in the saccharifying step is unnecessary.

After completion of the saccharifying step, the saccharified solution is preferably heated to 80° C., held at the same temperature for 30 minutes to 60 minutes, and then filtered using a filter such as a rotary vacuum filter and a filter press. The solution after filtration obtained by this method has a degree of coloring that is suppressed by about 10 to 30% compared with the solution after filtration obtained by a conventional production method, that is, a method of adding activated carbon after completion of a saccharifying step. This suppression effect can hardly be described only by the effect of having adjusted pH to a low level, and the coloring suppression effect has probably been enhanced compared with the conventional method by adding activated carbon in the liquefying and/or the saccharifying step. However, the reason is not apparent.

Further, it is preferred to add activated carbon in the liquefying step because a higher coloring suppression effect can be observed than adding activated carbon in the saccharifying step. Furthermore, it is preferred to add activated carbon to the liquefying step in which enzyme is not used because a higher coloring suppression effect is observed.

In addition, when activated carbon is added in the saccharifying step, it is preferred to add activated carbon to the saccharifying step performed by adding α-amylase in combination with glucoamylase because a higher coloring suppression effect is observed than adding activated carbon to the saccharifying step performed by adding glucoamylase alone.

The filtered solution can be optionally subjected to after-treatment based on a common production process. In the common after-treatment, the filtered solution is subjected to the steps of secondary decoloring and filtration by activated carbon, desalting by an ion-exchange resin, and separation of an indigestible fraction and a glucose fraction by a chromatography separation unit, a reverse osmosis membrane, or the like to obtain an indigestible fraction, and the indigestible fraction is further subjected to purification and concentration to produce a liquid product or pulverized by spray drying to produce indigestible dextrin. On the other hand, in the method for producing indigestible dextrin by the present invention, since the degree of coloring after filtration is suppressed to a low level as compared with a conventional production method, the amount of activated carbon used in secondary decoloring or tertiary decoloring is suppressed or the activated carbon is unnecessary as a result, and it is possible to extend the life of ion-exchange resin because the load of ion-exchange resin is reduced. Therefore, considerable cost reduction of the purification step and improvement in quality can be expected.

EXAMPLES

Hereinafter, the present invention will be described further in detail with reference to Examples, but the present invention is not limited thereto.

Example 1

Example (1) of Adding 1.5% of Activated Carbon During Saccharification

Water was added to pyrodextrin to obtain a 40 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto were added glucoamylase (AMG, manufactured by Novo Nordisk S/A) in an amount of 0.6 mass % relative to the solid content and zinc chloride-activated carbon (Carboraffin 20, manufactured by Japan EnviroChemicals, Ltd.) in an amount of 1.5 mass % relative to the solid content to perform saccharification and hydrolysis at 60° C. for 14 hours.

Then, the saccharified solution was heated to 80° C. and held for 60 minutes and then subjected to diatomaceous earth filtration. The degree of coloring of filtrate was 2.65. Further, the osmotic pressure and sugar composition (the amount of glucose produced) serving as indices of the degree of decomposition were substantially the same as those in Comparative Example 1 which is a conventional method (Table 1).

Comparative Example 1

Example (1) of Adding 1.5% of Activated Carbon After Saccharification

Water was added to pyrodextrin to obtain a 40 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, in order to match heating conditions with those in other experiments, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform saccharification and hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 1.5 mass % relative to the solid content. Then, the resulting mixture was held for 60 minutes and then subjected to diatomaceous earth filtration. The degree of coloring of filtrate was 2.92.

Example 2

Example (2) of Adding 1.5% of Activated Carbon During Saccharification

Water was added to pyrodextrin to obtain a 40 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content, glucoamylase (AMG, manufactured by Novo Nordisk S/A) in an amount of 0.6 mass % relative to the solid content, and zinc chloride-activated carbon (Carboraffin 20, manufactured by Japan EnviroChemicals, Ltd.) in an amount of 1.5 mass % relative to the solid content to perform saccharification and hydrolysis at 60° C. for 14 hours.

Then, the saccharified solution was heated to 80° C. and held for 60 minutes and then subjected to diatomaceous earth filtration. The degree of coloring of filtrate was 2.06. Further, the osmotic pressure and sugar composition (the amount of glucose produced) serving as indices of the degree of decomposition were substantially the same as those in Comparative Example 1 which is a conventional method (Table 1).

Comparative Example 2

Example (2) of Adding 1.5% of Activated Carbon after Saccharification

Water was added to pyrodextrin to obtain a 40 mass % mixture, and thereto was added sodium hydroxide to adjust pH to 4.5. The resulting mixture was then heated at 95° C. for 30 minutes to liquefy pyrodextrin. Subsequently, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform saccharification and hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 1.5 mass % relative to the solid content. Then, the resulting mixture was held for 60 minutes and then subjected to diatomaceous earth filtration. The degree of coloring of filtrate was 2.72.

TABLE 1

|  | Example 1 | Comparative Example 1 | Example 2 | Comparative Example 2 |
|---|---|---|---|---|
| Timing of addition of activated carbon | During saccharification | After saccharification | During saccharification | After saccharification |
| Amount of activated carbon (%) | 1.5 | 1.5 | 1.5 | 1.5 |
| Liquefying step |  |  |  |  |
| pH | 5.5 | 5.5 | 4.5 | 4.5 |
| α-Amylase | Added | Added | Not added | Not added |
| Temperature (° C.)/time (minutes) | 95/30 | 95/30 | 95/30 | 95/30 |
| Saccharifying step |  |  |  |  |
| pH | 4.5 | 4.5 | 4.5 | 4.5 |
| α-Amylase | Not added | Not added | Added | Added |
| Glucoamylase | Added | Added | Added | Added |
| Temperature (° C.)/time (hours) | 60/14 | 60/14 | 60/14 | 60/14 |
| Degree of coloring after diatomaceous earth filtration | 2.65 | 2.92 | 2.06 | 2.72 |
| Osmotic pressure (mOsm/kg) | 322 | 318 | 318 | 319 |
| Sugar composition |  |  |  |  |
| DP3+ | 53.8 | 54.1 | 53.8 | 53.6 |
| DP2 | 4.8 | 4.7 | 4.9 | 4.9 |
| Glucose | 39.7 | 39.4 | 39.6 | 39.7 |
| Others | 1.7 | 1.9 | 1.7 | 1.8 |

Example 3

Example (1) of Adding 2.0% of Activated Carbon During Liquefaction

Water was added to pyrodextrin to obtain a 35 mass % mixture, and thereto was added sodium hydroxide to adjust pH to 5.5. Then, thereto were added α-amylase (Termamyl, manufactured by Novo Nordisk S/A) in an amount of 0.1 mass % relative to the solid content and zinc chloride-activated carbon (Carboraffin 20, manufactured by Japan EnviroChemicals, Ltd.) in an amount of 2.0 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 1.73. Further, the osmotic pressure and sugar composition (the amount of glucose produced) serving as indices of the degree of decomposition were substantially the same as those in Comparative Examples 3 and 4 which are conventional methods (Table 2).

Example 4

Example (2) of Adding 2.0% of Activated Carbon During Liquefaction

Water was added to pyrodextrin to obtain a 35 mass % mixture, and thereto was added sodium hydroxide to adjust pH to 4.5. Then, thereto was added zinc chloride-activated carbon (Carboraffin 20, manufactured by Japan EnviroChemicals, Ltd.) in an amount of 2.0 mass % relative to the solid content, and the resulting mixture was heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform saccharification and hydrolysis at 60° C. for 14 hours. Then, the saccharified solution was heated to 80° C. and held for 60 minutes and then subjected to diatomaceous earth filtration. The degree of coloring of filtrate was 1.44, which was the lowest degree of coloring in Examples in which 2% of activated carbon was added. Further, the osmotic pressure and sugar composition (the amount of glucose produced) serving as indices of the degree of decomposition were substantially the same as those in Comparative Examples 3 and 4 which are conventional methods (Table 2).

Example 5

Example (1) of Adding 2.0% of Activated Carbon During Saccharification

Water was added to pyrodextrin to obtain a 35 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto were added glucoamylase (AMG, manufactured by Novo Nordisk S/A) in an amount of 0.6 mass % relative to the solid content and zinc chloride-activated carbon (Carboraffin 20, manufactured by Japan EnviroChemicals, Ltd.) in an amount of 2.0 mass % relative to the solid content to perform saccharification and hydrolysis at 60° C. for 14 hours.

Then, the saccharified solution was heated to 80° C. and held for 60 minutes and then subjected to diatomaceous earth filtration. The degree of coloring of filtrate was 1.94. Further, the osmotic pressure and sugar composition (the amount of glucose produced) serving as indices of the degree of decomposition were substantially the same as those in Comparative Examples 3 and 4 which are conventional methods (Table 2).

Example 6

Example (2) of Adding 2.0% of Activated Carbon During Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content, glucoamylase (AMG, manufactured by Novo Nordisk S/A) in an amount of 0.6 mass % relative to the solid content, and zinc chloride-activated carbon (Carboraffin 20, manufactured by Japan EnviroChemicals, Ltd.) in an amount of 2.0 mass % relative to the solid content to perform saccharification and hydrolysis at 60° C. for 14 hours.

Then, the saccharified solution was heated to 80° C. and held for 60 minutes and then subjected to diatomaceous earth filtration. The degree of coloring of filtrate was 1.59. Further, the osmotic pressure and sugar composition (the amount of glucose produced) serving as indices of the degree of decomposition were substantially the same as those in Comparative Examples 3 and 4 which are conventional methods (Table 2).

Comparative Example 3

Example (1) of Adding 2.0% of Activated Carbon after Saccharification

Water was added to pyrodextrin to obtain a 35 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform saccharification and hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 2.0 mass % relative to the solid content. Then, the resulting mixture was held for 60 minutes and then subjected to diatomaceous earth filtration. The degree of coloring of filtrate was 2.22.

Comparative Example 4

Example (2) of Adding 2.0% of Activated Carbon after Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 2.0 mass % relative to the solid content. Then, the resulting mixture was held for 60 minutes and then subjected to diatomaceous earth filtration. The degree of coloring of filtrate was 2.06.

TABLE 2

| | Example 3 | Example 4 | Example 5 | Example 6 | Comparative Example 3 | Comparative Example 4 |
|---|---|---|---|---|---|---|
| Timing of addition of activated carbon | During liquefaction | During liquefaction | During saccharification | During saccharification | After saccharification | After saccharification |
| Amount of activated carbon (%) | 2.0 | 2.0 | 2.0 | 2.0 | 2.0 | 2.0 |
| Liquefying step | | | | | | |
| pH | 5.5 | 4.5 | 5.5 | 4.5 | 5.5 | 4.5 |
| α-Amylase | Added | Not added | Added | Not added | Added | Not added |
| Temperature (° C.)/time (minutes) | 95/30 | 95/30 | 95/30 | 95/30 | 95/30 | 95/30 |
| Saccharifying step | | | | | | |
| pH | 4.5 | 4.5 | 4.5 | 4.5 | 4.5 | 4.5 |
| α-Amylase | Not added | Added | Not added | Added | Not added | Added |
| Glucoamylase | Added | Added | Added | Added | Added | Added |
| Temperature (° C.)/time (hours) | 60/14 | 60/14 | 60/14 | 60/14 | 60/14 | 60/14 |
| Degree of coloring after diatomaceous earth filtration | 1.73 | 1.44 | 1.94 | 1.59 | 2.22 | 2.06 |
| Osmotic pressure (mOsm/kg) | 319 | 322 | 317 | 322 | 319 | 319 |
| Sugar composition | | | | | | |
| DP3+ | 54.1 | 54.0 | 53.9 | 54.0 | 54.1 | 54.1 |
| DP2 | 4.6 | 4.6 | 4.6 | 4.6 | 4.5 | 4.6 |

TABLE 2-continued

|  | Example 3 | Example 4 | Example 5 | Example 6 | Comparative Example 3 | Comparative Example 4 |
|---|---|---|---|---|---|---|
| Glucose | 39.7 | 39.9 | 39.7 | 40.0 | 39.8 | 39.7 |
| Others | 1.6 | 1.6 | 1.8 | 1.5 | 1.6 | 1.6 |

Example 7

Load Test on Ion Exchange Resin

The filtrates obtained in Example 4 and Comparative Example 3 were passed, at SV=3, through a column filled with a mixture of 5 ml of cations (Amberlite 200CT, manufactured by ORGANO CORPORATION) and 10 ml of anions (Amberlite IRA900, manufactured by ORGANO CORPORATION). The passed solution was fractionated by every 1 g in terms of solids, and each fraction was measured for Brix, pH, electrical conductivity, and the degree of coloring. The analysis results of fractions 30 and 60 are shown in Table 3 The leakage of salts in an ion exchange step was suppressed, resulting in a small change in pH of the treated saccharide solution by performing the liquefying step and the saccharifying step in the presence of activated carbon. Therefore, when the same amount of saccharide solution is passed through, the load of ion exchange resin will be greatly reduced.

TABLE 3

|  | Filtrate of Example 4 | | | Filtrate of Comparative Example 3 | | |
|---|---|---|---|---|---|---|
| Analytical item | Stock solution | Fraction 30 | Fraction 60 | Stock solution | Fraction 30 | Fraction 60 |
| Brix | 27.4 | 27.4 | 27.4 | 27.4 | 27.5 | 27.4 |
| pH | 4.5 | 3.9 | 3.2 | 4.4 | 3.6 | 2.8 |
| Electrical conductivity (µS/cm) | 814 | 22 | 287 | 869 | 36 | 496 |
| Degree of coloring | 1.44 | 1.18 | 1.31 | 2.22 | 1.83 | 2.06 |

Example 8

Example (1) of Adding 3.0% of Activated Carbon During Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content, glucoamylase (AMG, manufactured by Novo Nordisk S/A) in an amount of 0.6 mass % relative to the solid content, and zinc chloride-activated carbon (Carboraffin 20, manufactured by Japan EnviroChemicals, Ltd.) in an amount of 3.0 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 1.00 Further, the osmotic pressure and sugar composition (the amount of glucose produced) serving as indices of the degree of decomposition were substantially the same as those in Comparative Examples 5 and 6 which are conventional methods (Table 4).

Comparative Example 5

Example (1) of Adding 3.0% of Activated Carbon after Saccharification

Water was added to pyrodextrin to obtain a 35 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 3.0 mass % relative to the solid content. Then, the resulting mixture was held for 60 minutes and then subjected to diatomaceous earth filtration. The degree of coloring of filtrate was 1.26.

Comparative Example 6

Example (2) of Adding 3.0% of Activated Carbon after Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 3.0 mass % relative to the solid content. Then, the resulting mixture was held for 60 minutes and then subjected to diatomaceous earth filtration. The degree of coloring of filtrate was 1.16.

TABLE 4

| | Example 8 | Comparative Example 5 | Comparative Example 6 |
|---|---|---|---|
| Timing of addition of activated carbon | During saccharification | After saccharification | After saccharification |
| Amount of activated carbon (%) | 3.0 | 3.0 | 3.0 |
| Liquefying step | | | |
| pH | 4.5 | 5.5 | 4.5 |
| α-Amylase | Not added | Added | Not added |
| Temperature (° C.)/time (minutes) | 95/30 | 95/30 | 95/30 |
| Saccharifying step | | | |
| pH | 4.5 | 4.5 | 4.5 |
| α-Amylase | Added | Not added | Added |
| Glucoamylase | Added | Added | Added |
| Temperature (° C.)/time (hours) | 60/14 | 60/14 | 60/14 |
| Degree of coloring after diatomaceous earth filtration | 1.00 | 1.26 | 1.16 |
| Osmotic pressure (mOsm/kg) | 327 | 322 | 324 |
| Sugar composition | | | |
| DP3+ | 53.4 | 53.6 | 53.4 |
| DP2 | 4.7 | 4.6 | 4.6 |
| Glucose | 40.2 | 40.2 | 40.3 |
| Others | 1.7 | 1.7 | 1.7 |

Example 9

Example (1) of Adding 4.0% of Activated Carbon During Liquefaction

Water was added to pyrodextrin to obtain a 35 mass % mixture, and thereto was added sodium hydroxide to adjust pH to 5.5. Then, thereto were added α-amylase (Termamyl, manufactured by Novo Nordisk S/A) in an amount of 0.1 mass % relative to the solid content and zinc chloride-activated carbon (Carboraffin 20, manufactured by Japan EnviroChemicals, Ltd.) in an amount of 4.0 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 0.69. Further, the osmotic pressure and sugar composition (the amount of glucose produced) serving as indices of the degree of decomposition were substantially the same as those in Comparative Examples 7 and 8 which are conventional methods (Table 5).

Example 10

Example (2) of Adding 4.0% of Activated Carbon During Liquefaction

Water was added to pyrodextrin to obtain a 35 mass % mixture, and thereto was added sodium hydroxide to adjust pH to 4.5. Then, thereto was added zinc chloride-activated carbon (Carboraffin 20, manufactured by Japan EnviroChemicals, Ltd.) in an amount of 4.0 mass % relative to the solid content, and the resulting mixture was heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 0.61. Further, the osmotic pressure and sugar composition (the amount of glucose produced) serving as indices of the degree of decomposition were substantially the same as those in Comparative Examples 7 and 8 which are conventional methods (Table 5).

Example 11

Example of Adding 4.0% of Activated Carbon During Saccharification

Water was added to pyrodextrin to obtain a 35 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto were added glucoamylase (AMG, manufactured by Novo Nordisk S/A) in an amount of 0.6 mass % relative to the solid content and zinc chloride-activated carbon (Carboraffin 20, manufactured by Japan EnviroChemicals, Ltd.) in an amount of 4.0 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 0.78. Further, the osmotic pressure and sugar composition (the amount of glucose produced) serving as indices of the degree of decomposition were substantially the same as those in Comparative Examples 7 and 8 which are conventional methods (Table 5).

Example 12

Example (2) of Adding 4.0% of Activated Carbon During Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content, glucoamylase (AMG, manufactured by Novo Nordisk S/A) in an amount of 0.6 mass % relative to the solid content, and zinc chloride-activated carbon (Carboraffin 20, manufactured by Japan EnviroChemicals, Ltd.) in an amount of 4.0 mass % relative to the solid content to perform hydrolysis at 60° C. for 14 hours.

Then, the saccharified solution was heated to 80° C. and held for 60 minutes and then subjected to diatomaceous earth filtration. The degree of coloring of filtrate was 0.68. Further, the osmotic pressure and sugar composition (the amount of glucose produced) serving as indices of the degree of decomposition were substantially the same as those in Comparative Examples 7 and 8 which are conventional methods (Table 5).

Comparative Example 7

Example of Adding 4.0% of Activated Carbon after Saccharification

Water was added to pyrodextrin to obtain a 35 mass % mixture, and thereto was added sodium hydroxide to adjust pH to 5.5. Then, thereto was added α-amylase (Termamyl, manufactured by Novo Nordisk S/A) in an amount of 0.1 mass % relative to the solid content, and the resulting mixture was heated at 95° C. for 30 minutes to liquefy pyrodextrin. Subsequently, the liquefied solution was held at 121° C. for 10 minutes to deactivate α-amylase.

Next, the temperature was cooled to 60° C., and pH was adjusted to 4.5 with sodium hydroxide and hydrochloric acid. Then, thereto was added glucoamylase (AMG, manufactured by Novo Nordisk S/A) in an amount of 0.6 mass % relative to the solid content to perform hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 4.0 mass % relative to the solid content. Then, the resulting mixture was held for 60 minutes and then subjected to diatomaceous earth filtration. The degree of coloring of filtrate was 0.86.

Comparative Example 8

Example (2) of Adding 4.0% of Activated Carbon after Saccharification

Water was added to pyrodextrin to obtain a 35 mass % mixture, and thereto was added sodium hydroxide to adjust pH to 4.5. The resulting mixture was then heated at 95° C. for 30 minutes to liquefy pyrodextrin. Subsequently, in order to match heating conditions with those in other experiments, the liquefied solution was held at 121° C. for 10 minutes.

Next, the temperature was cooled to 60° C., and pH was adjusted to 4.5 with sodium hydroxide and hydrochloric acid. Then, thereto were added α-amylase (Termamyl, manufactured by Novo Nordisk S/A) in an amount of 0.1 mass % relative to the solid content and glucoamylase (AMG, manufactured by Novo Nordisk S/A) in an amount of 0.6 mass % relative to the solid content to perform hydrolysis at 60° C. for 14 hours.

Then, the saccharified solution was heated to 80° C., and thereto was added zinc chloride-activated carbon (Carboraffin 20, manufactured by Japan EnviroChemicals, Ltd.) in an amount of 4.0 mass % relative to the solid content. Then, the resulting mixture was held for 60 minutes and then subjected to diatomaceous earth filtration. The degree of coloring of filtrate was 0.83.

TABLE 5

|  | Example 9 | Example 10 | Example 11 | Example 12 | Comparative Example 7 | Comparative Example 8 |
|---|---|---|---|---|---|---|
| Timing of addition of activated carbon | During liquefaction | During liquefaction | During saccharification | During saccharification | After saccharification | After saccharification |
| Amount of activated carbon (%) | 4.0 | 4.0 | 4.0 | 4.0 | 4.0 | 4.0 |
| Liquefying step |  |  |  |  |  |  |
| pH | 5.5 | 4.5 | 5.5 | 4.5 | 5.5 | 4.5 |
| α-Amylase | Added | Not added | Added | Not added | Added | Not added |
| Temperature (° C.)/time (minutes) | 95/30 | 95/30 | 95/30 | 95/30 | 95/30 | 95/30 |
| Saccharifying step |  |  |  |  |  |  |
| pH | 4.5 | 4.5 | 4.5 | 4.5 | 4.5 | 4.5 |
| α-Amylase | Not added | Added | Not added | Added | Not added | Added |
| Glucoamylase | Added | Added | Added | Added | Added | Added |
| Temperature (° C.)/time (hours) | 60/14 | 60/14 | 60/14 | 60/14 | 60/14 | 60/14 |
| Degree of coloring after diatomaceous earth filtration | 0.69 | 0.61 | 0.78 | 0.68 | 0.86 | 0.83 |
| Osmotic pressure (mOsm/kg) | 326 | 330 | 332 | 330 | 330 | 329 |
| Sugar composition |  |  |  |  |  |  |
| DP3+ | 53.7 | 53.5 | 53.3 | 53.2 | 53.1 | 53.1 |
| DP2 | 4.5 | 4.5 | 4.4 | 4.7 | 4.7 | 4.7 |
| Glucose | 40.1 | 40.3 | 40.4 | 40.6 | 40.5 | 40.4 |
| Others | 1.7 | 1.8 | 1.9 | 1.6 | 1.7 | 1.6 |

What is claimed is:

1. A method for producing decolorized indigestible dextrin comprising the steps of liquefying pyrodextrin and saccharifying pyrodextrin in the presence of activated carbon, wherein the step of liquefying pyrodextrin with or without an enzyme is performed by heating an aqueous solution of pyrodextrin at 80° C. to 115° C. for period of 15 to 60 minutes in the presence of 0.1 to 5.0 mass % activated carbon relative to solid content in the reaction solution.

2. The method according to claim 1, wherein the step of saccharifying pyrodextrin is a step of hydrolyzing the liquefied solution of pyrodextrin using glucoamylase in combination with α-amylase.

3. The method according to claim 1, wherein the step of liquefying the pyrodextrin without the enzyme further comprises heating the aqueous solution of pyrodextrin at an adjusted pH of 4.3-4.5.

4. The method according to claim 1, wherein the amount of activated carbon is 1.0 to 2.5 mass % relative to solid content in the reaction solution.

* * * * *